US012597521B2

(12) United States Patent
Lee

(10) Patent No.: US 12,597,521 B2
(45) Date of Patent: Apr. 7, 2026

(54) SURVEY-BASED DIAGNOSIS METHOD AND SYSTEM THEREFOR

(71) Applicant: UNIVERSITY-INDUSTRY COOPERATION GROUP OF KYUNG HEE UNIVERSITY, Yongin-si (KR)

(72) Inventor: Jae Dong Lee, Seoul (KR)

(73) Assignee: UNIVERSITY-INDUSTRY COOPERATION GROUP OF KYUNG HEE UNIVERSITY, Yongin-si (KR)

( * ) Notice: Subject to any disclaimer, the term of this patent is extended or adjusted under 35 U.S.C. 154(b) by 0 days.

(21) Appl. No.: 18/833,163

(22) PCT Filed: Dec. 7, 2022

(86) PCT No.: PCT/KR2022/019830
§ 371 (c)(1),
(2) Date: Jul. 25, 2024

(87) PCT Pub. No.: WO2023/146120
PCT Pub. Date: Aug. 3, 2023

(65) Prior Publication Data
US 2025/0118434 A1 Apr. 10, 2025

(30) Foreign Application Priority Data
Jan. 25, 2022 (KR) ........................ 10-2022-0010737

(51) Int. Cl.
G16H 50/20 (2018.01)
G16H 10/20 (2018.01)
(52) U.S. Cl.
CPC ............. G16H 50/20 (2018.01); G16H 10/20 (2018.01)

(58) Field of Classification Search
None
See application file for complete search history.

(56) References Cited

U.S. PATENT DOCUMENTS

2003/0055679 A1* 3/2003 Soll ........................ G16H 40/20
705/2
2006/0122465 A1* 6/2006 Bastien .................. G16H 50/70
128/920
(Continued)

FOREIGN PATENT DOCUMENTS

JP          4897937 B2      3/2012
KR   10-2010-0034969 A     4/2010
(Continued)

OTHER PUBLICATIONS

Babu, A. Hari, "Latent Space Data Augmentation for Facial Diagnosis from Face Images of Multiple Diseases," 2021 2nd International Conference on Computational Methods in Science & Technology (Year: 2021).*
(Continued)

*Primary Examiner* — John P Go
(74) *Attorney, Agent, or Firm* — Sughrue Mion, PLLC

(57) ABSTRACT

A survey-based diagnosis method and a system therefor are provided. The survey-based diagnosis method according to several embodiments of the present disclosure enables a diagnosee to be diagnosed on the basis of response information about the diagnosee with respect to a plurality of survey questions. The plurality of survey questions can include questions for diagnosing an energy and blood generation function, an energy and blood circulation function, and an energy and blood balance adjustment function, and the health condition of the diagnosee can be accurately diagnosed by using these questions. In addition, a quick and
(Continued)

convenient oriental medicine diagnosis service can be provided using a questionnaire technique.

9 Claims, 8 Drawing Sheets

(56)                References Cited

U.S. PATENT DOCUMENTS

| | | | | |
|---|---|---|---|---|
| 2012/0290324 | A1* | 11/2012 | Ribbing | G16H 70/20 |
| | | | | 705/3 |
| 2021/0183525 | A1* | 6/2021 | Overhage | G16H 50/70 |
| 2021/0295105 | A1* | 9/2021 | Sallee | G06V 10/82 |
| 2021/0327562 | A1* | 10/2021 | Kushwah | G06T 7/0016 |

FOREIGN PATENT DOCUMENTS

| | | | |
|---|---|---|---|
| KR | 10-2116664 | B1 | 5/2020 |
| KR | 10-2020-0080290 | A | 7/2020 |
| KR | 10-2021-0055897 | A | 5/2021 |

OTHER PUBLICATIONS

Escolano, Carlos, "Training Multilingual Machine Translation by Alternately Freezing Language-Specific Encoders-Decoders," TALP Research Center, May 2020 (Year: 2020).*
International Search Report for PCT/KR2022/019830 dated Apr. 3, 2023.

* cited by examiner

【Fig. 1】
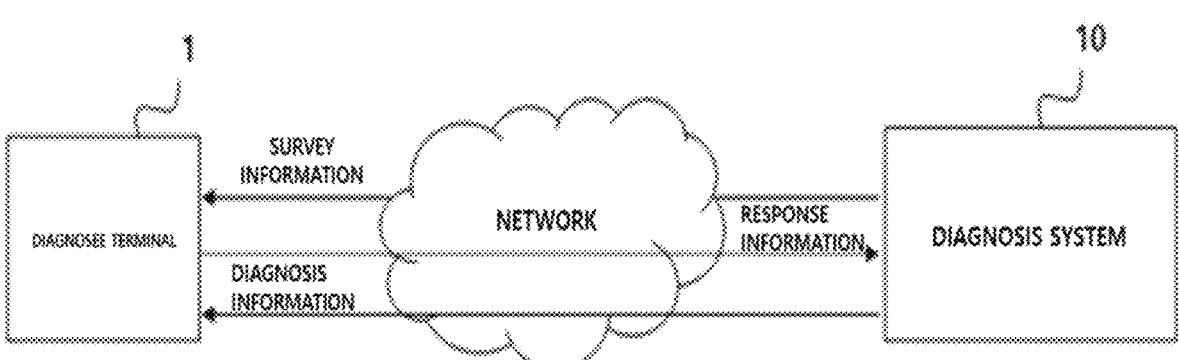
【Fig. 2】
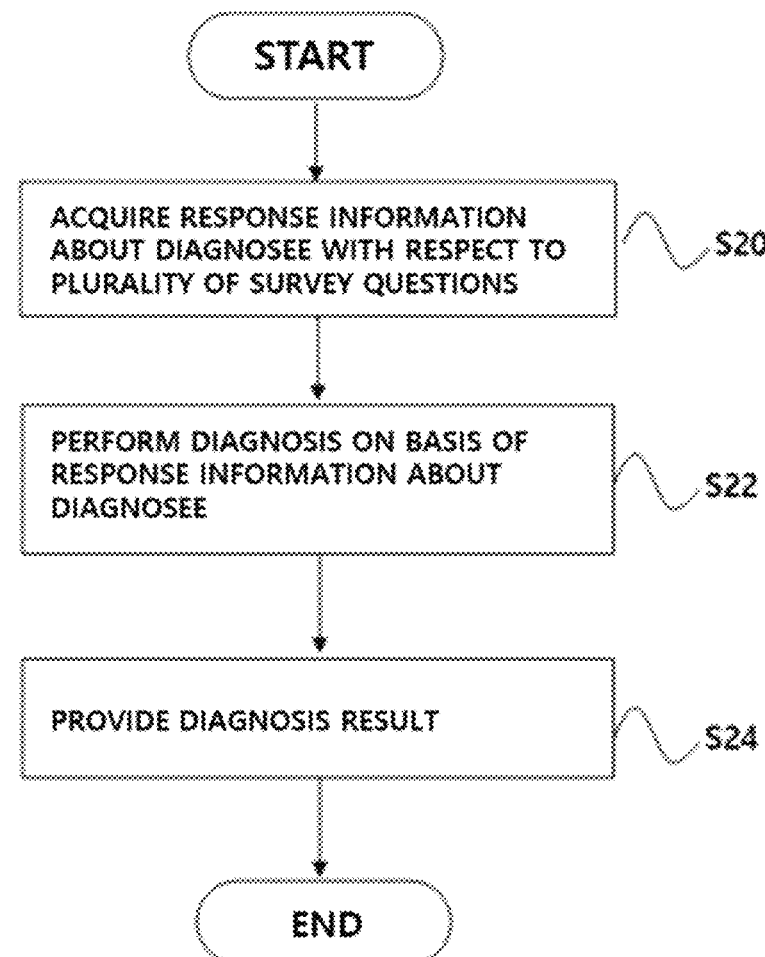

【Fig. 3】
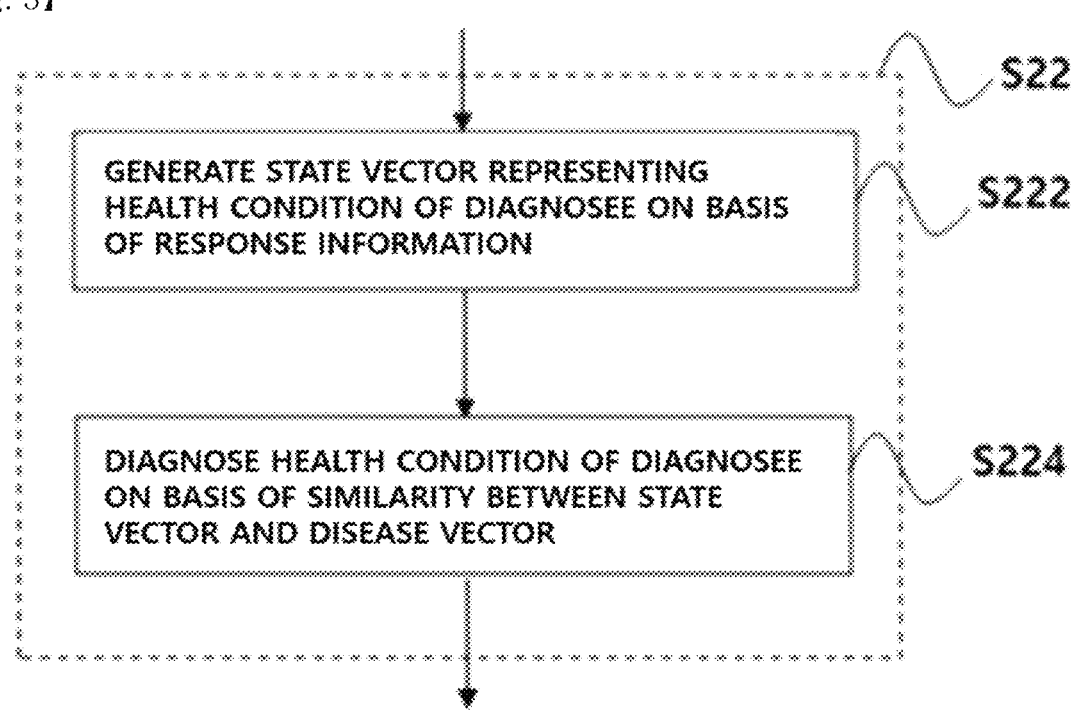
【Fig. 4】
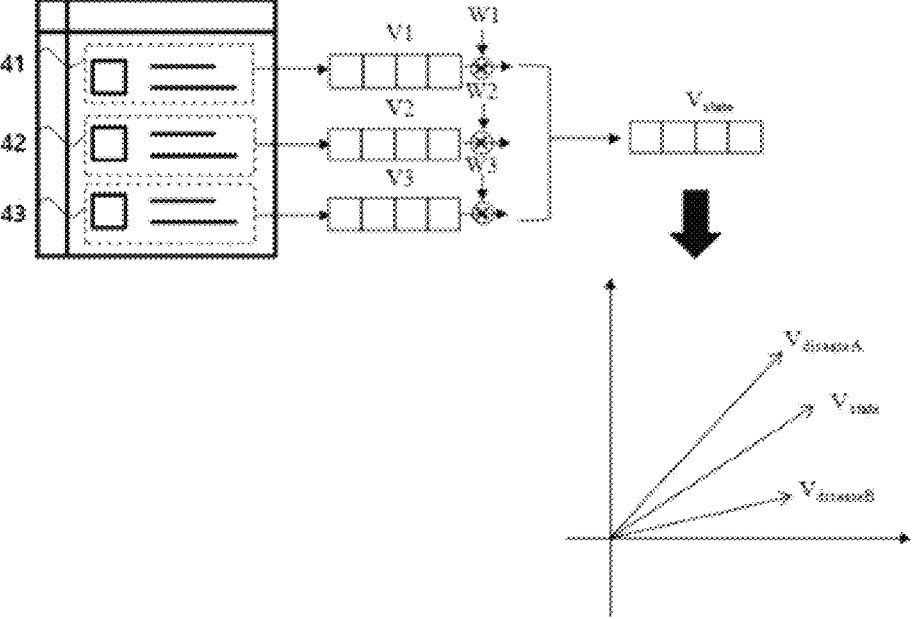

【Fig. 5】
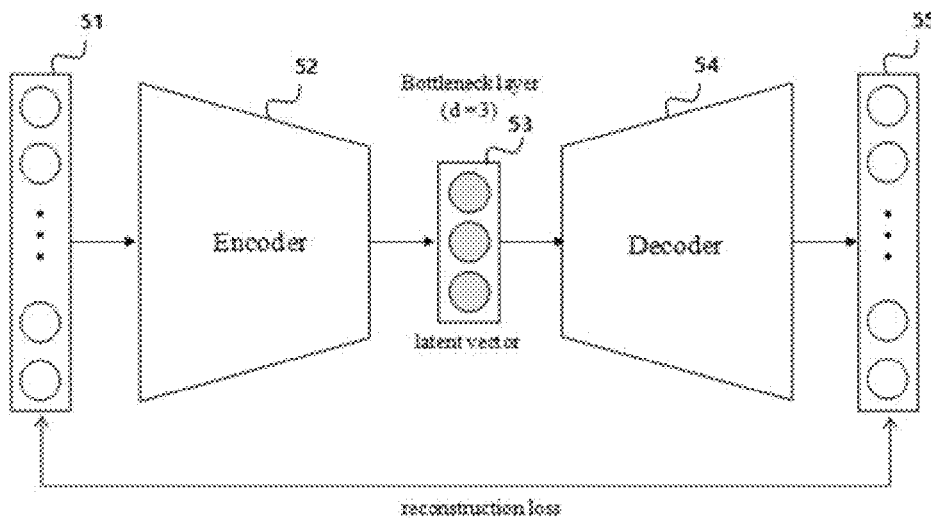
【Fig. 6】
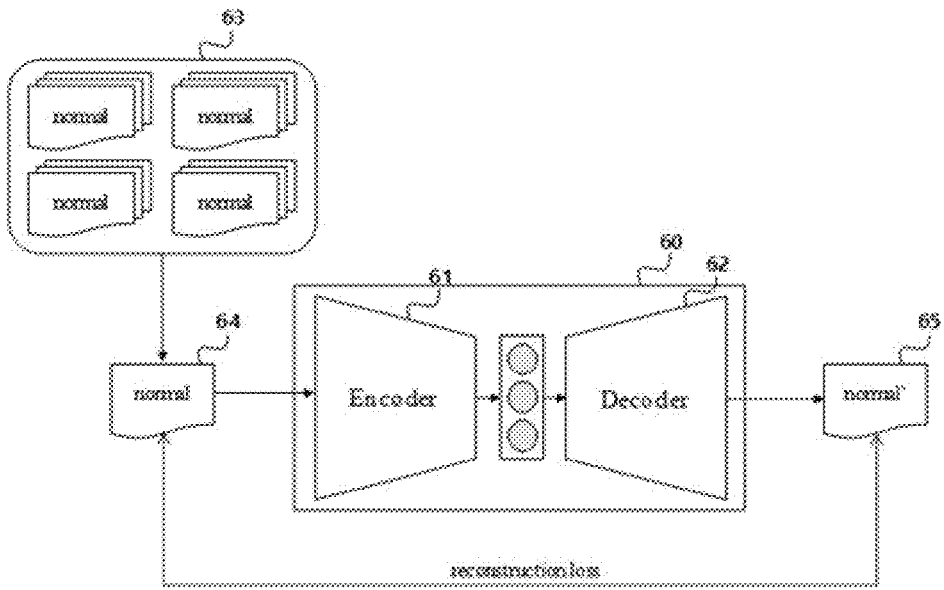

【Fig. 7】
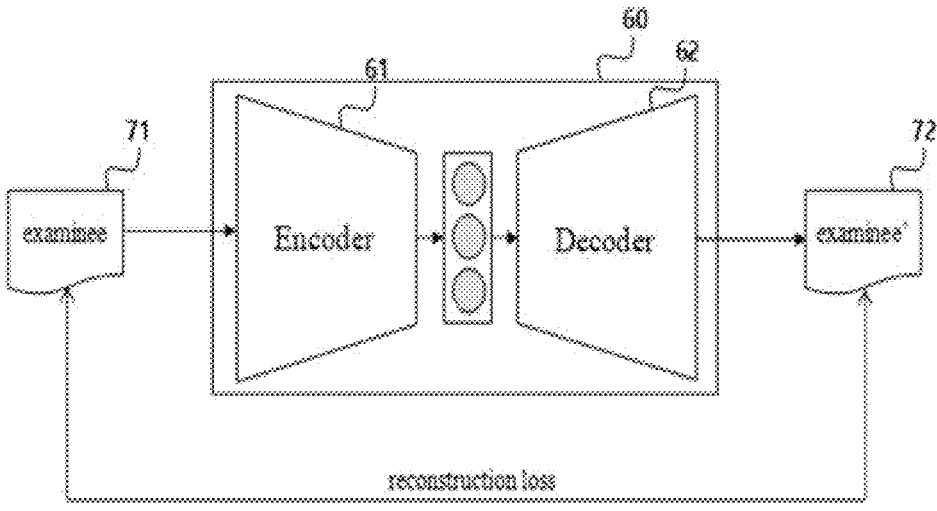
【Fig. 8】
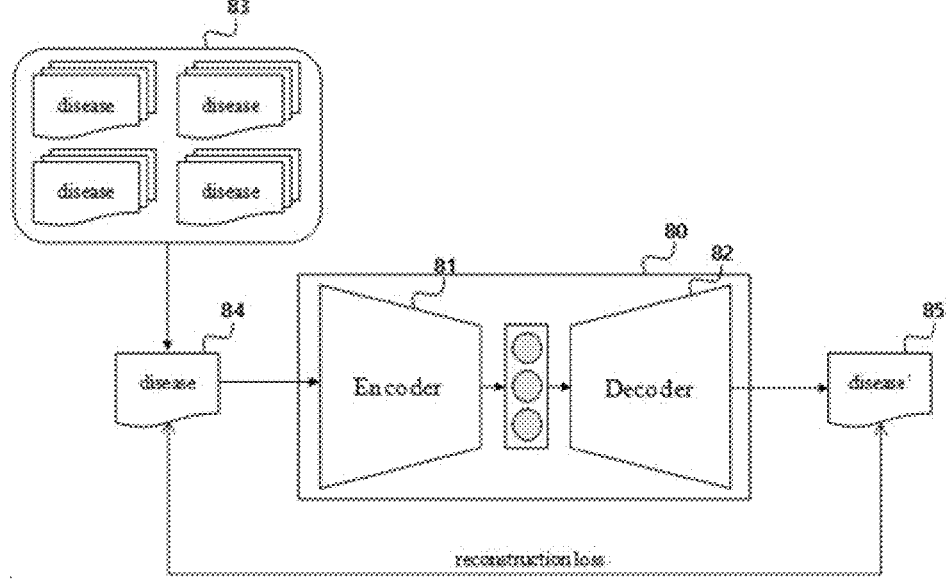

【Fig. 9】
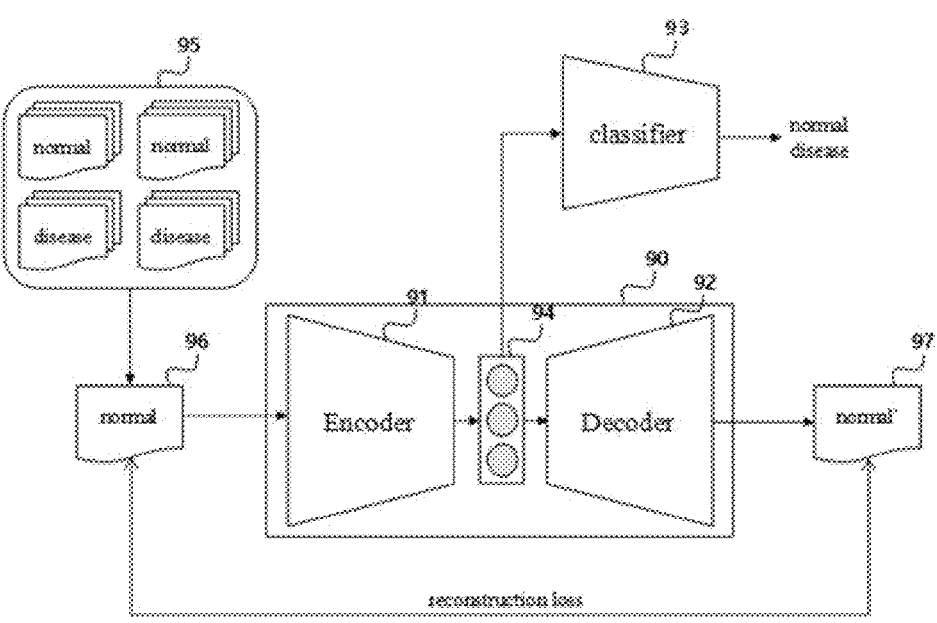

【Fig. 10】
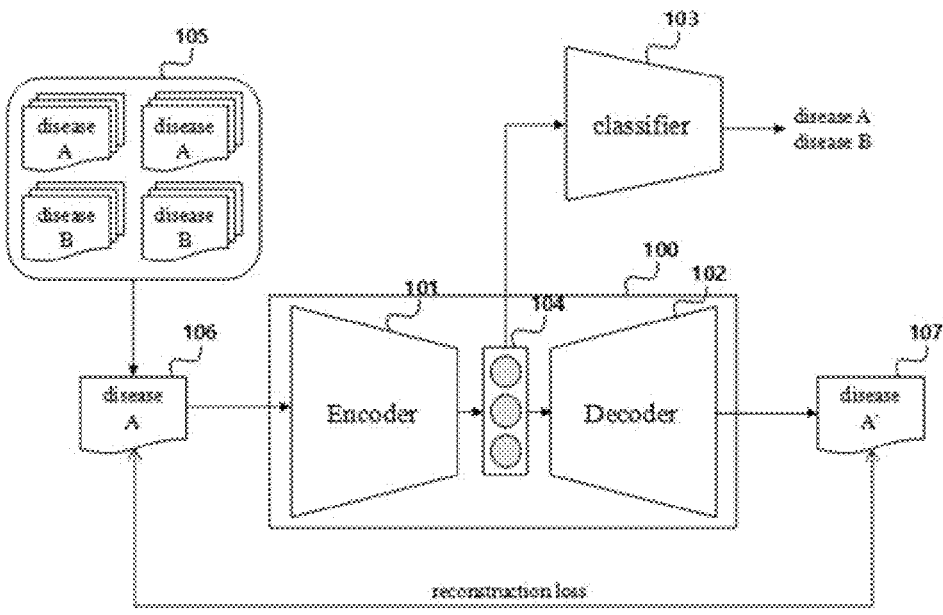

【Fig. 11】
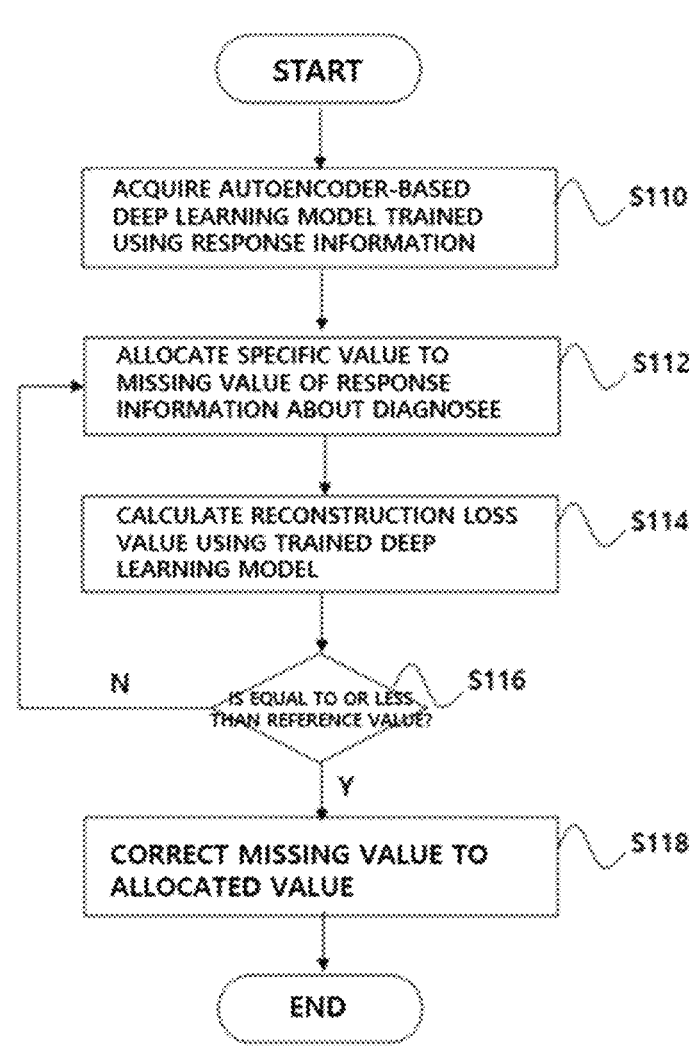

【Fig. 12】
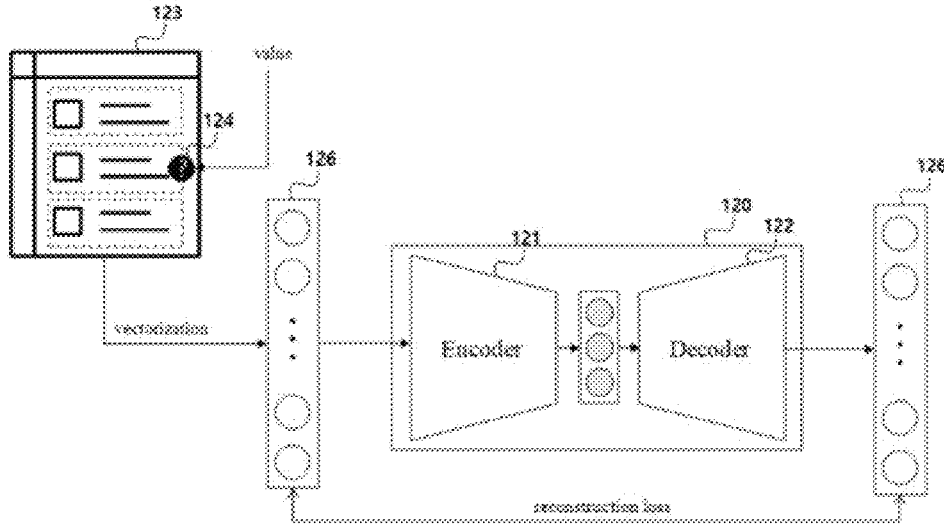
【Fig. 13】
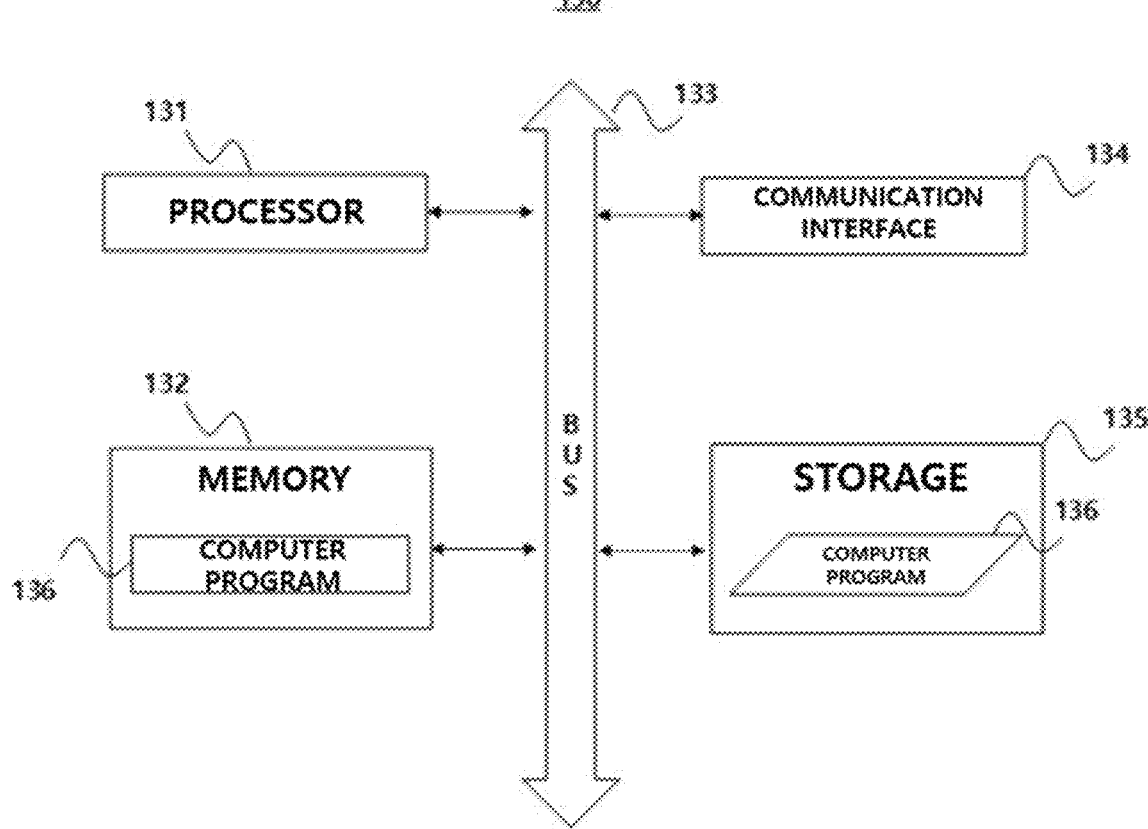

SURVEY-BASED DIAGNOSIS METHOD AND SYSTEM THEREFOR

CROSS REFERENCE TO RELATED APPLICATIONS

This application is a National Stage of International Application No. PCT/KR2022/019830 filed Dec. 7, 2022, claiming priority based on Korean Patent Application No. 10-2022-0010737 filed Jan. 25, 2022, the entire disclosures of which are incorporated herein by reference.

TECHNICAL FIELD

The present disclosure relates to a survey-based diagnosis method and a system thereof, and more particularly, to a method for performing an oriental medicine diagnosis using response information to a survey and a system for performing the method.

BACKGROUND ART

Oriental medicine is medicine that has been used to diagnose and treat the Korean body since ancient times, and is a scientific medicine that may diagnose and prescribe diseases according to unique physical characteristics of Korean while data suitable for our bodies have been accumulated over hundreds of years unlike Western medicine. Unlike Western medicine, the oriental medicine is not widely popularized and has been distant with the general public, but recently, has grown worldwide while interest in alternative medicine has been increased.

Meanwhile, a survey technique is one of commonly used techniques in a process of diagnosing the health condition of a diagnosee. For example, an oriental medicine specialist may provide a diagnosee with a questionnaire consisting of a plurality of survey questions, and roughly determine the health condition of the diagnosee based on response information written in the questionnaire. However, it is very difficult to accurately diagnose the health condition of the diagnosee (e.g., presence or absence of disease, type of disease, etc.) using only the survey technique due to difficulties in designing the survey questions, and accordingly, the areas in which the survey technique is utilized in the diagnostic process are still very limited.

DISCLOSURE

Technical Problem

An object to be solved by several embodiments of the present disclosure is to provide a method capable of accurately diagnosing a health condition of a diagnosee based on a survey and a system for performing the method.

The technical objects of the present disclosure are not restricted to the aforementioned technical objects, and other objects of the present disclosure, which are not mentioned above, will become more apparent to one of ordinary skill in the art to which the present disclosure pertains by referencing the detailed description of the present disclosure given below.

Technical Solution

In order to achieve the above aspects, a survey-based diagnosis method according to several embodiment of the present disclosure is a survey-based diagnosis method performed by at least one computing device, and may include acquiring response information about a diagnosee with respect to a plurality of survey questions and performing a diagnose on the diagnosee based on the acquired response information. At this time, the plurality of survey questions may include a first survey question for diagnosing an energy and blood generation function, a second survey question for diagnosing an energy and blood circulation function, and a third survey question for diagnosing an energy and blood balance adjustment function.

In an embodiment, the performing of the diagnosis may include generating a state vector representing a health condition of the diagnosee based on the response information, and diagnosing the health condition of the diagnosee based on similarity between the generated state vector and a disease vector.

In an embodiment, the performing of the diagnosis may include acquiring an autoencoder-based deep learning model trained using response information about a normal class with respect to the plurality of survey questions, calculating a reconstruction loss value for the acquired response information using the acquired deep learning model, and diagnosing the health condition of the diagnosee based on the calculated reconstruction loss value.

In an embodiment, the acquired response information may include a missing value for a specific survey question, and the performing of the diagnosis may include acquiring an autoencoder-based deep learning model trained using response information with respect to the plurality of survey questions, allocating a specific value to the missing value, calculating a reconstruction loss value for the response information allocated with the specific value using the acquired deep learning model, correcting the missing value to the specific value in response to the determination that the calculated reconstruction loss value is less than or equal to a reference value, and performing the correction of the diagnosee based on the response information with the corrected missing value.

In order to achieve the above aspects, a survey-based diagnosis system according to several embodiments of the present disclosure may include one or more processors and a memory for storing one or more instructions. At this time, the one or more processors may execute one or more of the stored instructions to perform an operation of acquiring response information about a diagnosee with respect to a plurality of survey questions and an operation of performing a diagnosis for the diagnosee based on the acquired response information. At this time, the plurality of survey questions may include a first survey question for diagnosing an energy and blood generation function, a second survey question for diagnosing an energy and blood circulation function, and a third survey question for diagnosing an energy and blood balance adjustment function.

In order to achieve the above aspects, a computer program according to several embodiments of the present disclosure may be connected with a computing device and stored in a computer-readable recording medium to execute steps of acquiring response information about a diagnosee with respect to a plurality of survey questions and performing a diagnosis for the diagnosee based on the acquired response information. At this time, the plurality of survey questions may include a first survey question for diagnosing an energy and blood generation function, a second survey question for diagnosing an energy and blood circulation function, and a third survey question for diagnosing an energy and blood balance adjustment function.

Advantageous Effects

According to various embodiments of the present disclosure, it is possible to diagnose the health condition of a diagnosee using a plurality of survey questions for diagnosing energy and blood generation function, circulation function, and balance adjustment function. From an oriental medicine viewpoint, since most diseases are caused by problems with the functions, it is possible to accurately diagnose the health condition of a diagnosee by using survey questions for diagnosing these functions. Furthermore, it is possible to provide a quick and convenient oriental medicine diagnosis service to a diagnosee by using a survey technique.

Further, it is possible to generate a state vector representing the health condition from response information about a diagnosee and diagnose the health condition of the diagnosee base on similarity between the state vector and a disease vector. Accordingly, it is possible to further improve reliability and accuracy of diagnostic results.

Further, it is possible to more accurately diagnose the health condition of a diagnosee by using a reconstruction loss value of an autoencoder-based deep learning model trained using response information about a normal class or patient class.

Further, it is possible to accurately correct a missing value in response information about a diagnosee by using a reconstruction loss value of an autoencoder-based deep learning model.

The effects of the present disclosure are not limited to the aforementioned effect, and other effects, which are not mentioned above, will be apparent to a person having ordinary skill in the art from the following disclosure.

DESCRIPTION OF DRAWINGS

FIG. 1 is an exemplary diagram for describing a survey-based diagnosis system and a service provision environment thereof according to several embodiments of the present disclosure.

FIG. 2 is an exemplary flowchart schematically illustrating a survey-based diagnosis method according to several embodiments of the present disclosure.

FIGS. 3 to 5 are exemplary diagrams for describing a diagnosis method according to an embodiment of the present disclosure.

FIG. 6 is an exemplary diagram for describing a diagnosis method according to another embodiment of the present disclosure.

FIG. 7 is an exemplary diagram for describing a diagnosis method according to yet another embodiment of the present disclosure.

FIG. 8 is an exemplary diagram for describing a diagnosis method according to yet another embodiment of the present disclosure.

FIG. 9 is an exemplary diagram for describing a diagnosis method according to yet another embodiment of the present disclosure.

FIG. 10 is an exemplary diagram for describing a diagnosis method according to yet another embodiment of the present disclosure.

FIGS. 11 and 12 are exemplary diagrams for describing a missing value correction method according to an embodiment of the present disclosure.

FIG. 13 illustrates an exemplary computing device capable of implementing a survey-based diagnosis system according to several embodiments of the present disclosure.

BEST MODES OF THE INVENTION

Hereinafter, preferred embodiments of the present disclosure will be described in detail with reference to the accompanying drawings. Advantages and features of the present disclosure, and methods for accomplishing the same will be more clearly understood from exemplary embodiments described in detail below with reference to the accompanying drawings. However, the technical idea of the present disclosure is not limited to the embodiments set forth below, and may be embodied in various different forms. The following embodiments are just for rendering the technical idea of the present disclosure complete and are set forth to provide a complete understanding of the scope of the present disclosure to a person with ordinary skill in the art to which the present disclosure pertains, and the technical idea of the present disclosure will only be defined by the scope of the claims.

When reference numerals refer to components of each drawing, it is to be noted that although like components are illustrated in different drawings, like components are denoted by the same reference numerals as possible. In the following description of the present disclosure, a detailed explanation of related known configurations or functions may be omitted to avoid obscuring the subject matter of the present disclosure.

Unless otherwise defined, all terms (including technical and scientific terms) used in the present specification may be used as the meaning which may be commonly understood by the person with ordinary skill in the art to which the present disclosure pertains. Terms defined in commonly used dictionaries should not be interpreted in an idealized or excessive sense unless expressly and specifically defined. It is also to be understood that the terminology used in this specification is for the purpose of describing embodiments only and is not intended to limit the present disclosure. Unless particularly stated otherwise in the present specification, a singular form also includes a plural form.

In describing the components of the embodiments of the present disclosure, terms including first, second, A, B, (a), (b), and the like may be used. These terms are just intended to distinguish the components from other components, and the terms do not limit the nature, sequence, or order of the components. When it is disclosed that any component is "connected", "coupled", or "linked" to other components, it should be understood that the component may be directly connected or linked to other components, but another component may be "connected", "coupled", or "linked" between the respective components.

It is to be understood that the terms "comprises" and/or "comprising" used in the specification are intended to be inclusive in a manner that does not exclude the presence of stated components, steps, operations, and/or elements does not exclude the addition.

Hereinafter, various embodiments of the present disclosure will be described in detail with reference to the accompanying drawings.

Modes of the Invention

FIG. 1 is an exemplary diagram for describing a survey-based diagnosis system 10 and a service provision environment thereof according to several embodiments of the present disclosure.

As illustrated in FIG. 1, the survey-based diagnosis system 10 may be a system that performs an oriental medicine diagnosis or provides an oriental medicine diagnosis service based on a survey. For example, the survey-based diagnosis system 10 may provide survey information including a plurality of survey questions to a diagnosee terminal 1, receive response information about the survey from the diagnosee terminal 1, and perform a diagnosis on the diagnosee based on the received response information. Hereinafter, for convenience of explanation, the survey-based diagnosis system 10 will be abbreviated as a "diagnosis system 10".

The survey information may include various questions, response items, and other information (e.g., scores, weights, etc.) designed to accurately and precisely diagnose the health condition of the diagnosee in terms of the oriental medicine. For example, the survey information may include a plurality of survey questions to diagnose energy and blood generation function, circulation function, and balance adjustment function. An accurate and precise diagnosis may be made on the diagnosee by using these survey questions, which is because most diseases are caused by problems with the energy and blood generation, circulation, and balance adjustment functions in terms of the oriental medicine.

The specific diagnosis operation of the diagnosis system 10 will be described in detail later with reference to the drawings below FIG. 2.

The diagnosis system 10 may be implemented with at least one computing device. For example, the diagnosis system 10 may be implemented with one computing device. As another example, the diagnosis system 10 may be implemented with a plurality of computing devices, but a first function of the diagnosis system 10 may be implemented in a first computing device and a second function may be implemented in a second computing device. Alternatively, a specific function of the diagnosis system 10 may also be implemented in a plurality of computing devices.

The computing device may be any device having a computing (processing) function regardless of a type, and an example of such a device will be described below with reference to FIG. 13.

The diagnosee terminal 1 is a terminal carried by the diagnosee (e.g., patient) and may be implemented with any computing device.

As illustrated in the drawing, the diagnosee terminal 1 and the diagnosis system 10 may communicate with each other via a network. Here, the network may be implemented as all types of wired/wireless networks, such as a Local Area Network (LAN), a Wide Area Network (WAN), a mobile radio communication network, and Wireless Broadband Internet (Wibro).

So far, the diagnosis system 10 and an exemplary service provision environment thereof according to several embodiments of the present disclosure have been described with reference to FIG. 1. Hereinafter, a survey-based diagnosis method that may be performed in the diagnosis system 10 illustrated in FIG. 1 will be described in detail.

The survey-based diagnosis method to be described below may be performed by at least one computing device. In other words, the method to be described below may be implemented by one or more instructions that may be executed by at least one computing device (or processor). Hereinafter, for providing the convenience of understanding, the description will be followed assuming that the method to be described below is performed in the diagnosis system 10 of the environment illustrated in FIG. 1. Accordingly, if a subject of a specific step (operation) is omitted, it should be understood that the method is performed by the diagnosis system 10. Of course, in a real environment, some steps of the method to be described below may also be performed on other computing devices.

FIG. 2 is an exemplary flowchart schematically illustrating a survey-based diagnosis method according to several embodiments of the present disclosure. However, it is only a preferred embodiment for achieving the object of the present disclosure, and it is obvious that some steps may be added or deleted as necessary.

As illustrated in FIG. 2, the embodiment may start in step S20 of acquiring response information about a diagnosee with respect to a plurality of survey questions. For example, the diagnosis system 10 may provide survey information including the plurality of survey questions to the diagnosee terminal 1 and acquire response information to the survey from the diagnosee terminal 1.

The plurality of survey questions may include questions for diagnosing energy and blood generation function, circulation function, and balance adjustment function. However, the present disclosure is not limited thereto. Examples of survey questions, response items, and scores for diagnosing these functions will refer to Tables 1 to 3 below. Tables 1 to 3 are related to the energy and blood generation, circulation, and balance adjustment functions, respectively. Hereinafter, unless otherwise stated, the survey questions on the energy and blood generation function are referred to as "first survey question", the survey questions on the energy and blood circulation function are referred to as "second survey question", and the survey questions on the energy and blood balance adjustment function are referred to as "third survey question".

TABLE 1

| Item (Total score) | Response item | Score by item |
|---|---|---|
| Usual digestive condition (30) | Always indigestion | 30 |
| | Sometimes indigestion | 20 |
| | No digestive discomfort | 0 |
| Usual number of meals (20) | 1 meal or less per day | 20 |
| | Two meals per day | 10 |
| | 3 meals or more per day | 0 |
| Weight (BMI) (20) | BMI 14.9 or less | 20 |
| | BMI 15 to 19 | 10 |
| | BMI 20 or more | 0 |
| Heat evaluation (10) | Usually cold hands and feet | 5 |
| | Usually likes warm food | 5 |
| Usual personality (10) | Timid in everything | 5 |
| | Usually introvertive | 5 |
| Abdominal condition (10) | The costal angle in the abdomen is an acute angle of 90 degrees or less | 5 |
| | There is no strength when the abdomen is pressed with the hand | 5 |

TABLE 2

| Item (Total score) | Response item | Score by item |
|---|---|---|
| Weight (BMI) (40) | BMI 35 or more | 40 |
| | BMI 34.9 to 25 | 30 |
| | BMI 25 or more | 0 |
| Waist circumference (10) | Men 90 cm or higher, Women 85 cm or higher | 10 |
| Pulse rate for 1 min (20) | 60 or less | 20 |
| | 60 to 80 | 10 |
| | 80 or more | 0 |
| Weight (BMI) (40) | BMI 35 or more | 40 |
| | BMI 34.9 to 25 | 30 |
| | BMI 25 or more | 0 |
| Waist circumference | Men 90 cm or higher, | 10 |

TABLE 2-continued

| Item (Total score) | Response item | Score by item |
|---|---|---|
| (10) | Women 85 cm or higher | |
| Pulse rate for | 60 or less | 20 |
| 1 min (20) | 60 to 80 | 10 |
| | 80 or more | 0 |

TABLE 3

| Item (Total score) | Response item | Score by item |
|---|---|---|
| Number of wake-up times during sleep (20) | 3 times or more | 20 |
| | 1 to 2 times | 10 |
| | 0 time | 0 |
| Other sleep states (20) | Bed time is after midnight | 5 |
| | Bed time is irregular | 5 |
| | Wake-up time in the morning is after 8 a.m. | 5 |
| | Total sleep time is irregular | 5 |
| Pulse rate for 1 min (20) | 100 or more | 20 |
| | 80 to 100 | 10 |
| | 80 or less | 0 |
| Upper and lower body ratio in body type (10) | Chest circumference/hip circumference >= average | 5 |
| | Neck circumference/calf circumference >= average | 5 |
| Heat evaluation (15) | Usually feel hot in face | 5 |
| | Feet below waist are cold | 5 |
| | Usually like cold food | 5 |
| Usual activity habits (5) | Usually move around a lot | 5 |
| Usual personality (5) | Usual personality is extrovertive or impatient | 5 |
| Abdominal condition (5) | Feel tense when pressing abdomen with hand | 5 |

Meanwhile, in an embodiment, it may be determined whether there is a missing value in the response information about the diagnosee before performing the diagnosis. In addition, in response to the determination that there is the missing value, the missing value may be corrected using an autoencoder-based deep learning model. Accordingly, the convenience of the diagnosee may be improved, and the embodiment will be described in detail later with reference to FIGS. 11 and 12.

In step S22, the diagnosis may be performed based on the response information about the diagnosee. For example, the diagnosis system 10 may diagnose the energy and blood generation function based on the response information to the first survey question (e.g., if the total score of the response items is 50 points or more, it is determined that there is a problem in the corresponding function), diagnose the energy and blood circulation function based on the response information to the second survey question, and diagnose the energy and blood balance adjustment function based on the response information to the third survey question. In addition, the diagnosis system 10 may diagnose the health condition (e.g., presence or absence of disease, type of disease) of the diagnosee by considering the problematic function. Examples of diseases associated with the problematic function will refer to Table 4 below. As another example, the diagnosis system 10 may also diagnose the health condition of the diagnosee by comprehensively considering response information about the energy and blood generation function, circulation function, and adjustment function.

TABLE 4

| Classification | Associated diseases |
|---|---|
| Energy and blood generation function | Dementia, Parkinson's disease, amnesia, acute and chronic digestive diseases, chronic fatigue, low blood pressure, tinnitus (Meniere), decreased vision, vertigo, headache, Raynauds syndrome, shoulder pain |
| Energy and blood circulation function | Obesity, metabolic diseases (hyperlipidemia, blood pressure, diabetes), heart disease, stroke, respiratory disease, arthritis, back pain (disk, stenosis), autoimmune diseases (rheumatism, fibromyalgia, ankylosing spondylitis), various cancers, etc. |
| Energy and blood balance adjustment function | Reproductive diseases, infertility (sterility), endocrine diseases (thyroid hormones, etc.), urinary diseases (urinary disorders), hair loss, dry eyes, skin diseases (psoriasis), headache, tinnitus, mental illness (insomnia, panic disorder, depression), back pain (disk, stenosis), arthritis, plantar fasciitis, etc. |

In an embodiment, the diagnosis system 10 may provide the diagnosee with additional survey information for diagnosing diseases associated with the problematic function, and also predict diseases associated with the diagnosee based on the response information to the additional survey.

Meanwhile, the specific method of performing the diagnosis may vary depending on an embodiment.

In an embodiment, the health condition of the diagnosee may be diagnosed based on the similarity between a state vector generated based on response information about the diagnosee (i.e., a vector representing the health condition of the diagnosee) and a disease vector. The embodiment will be described below with reference to FIGS. 3 to 5.

In another embodiment, the health condition of the diagnosee may be diagnosed using an autoencoder-based deep learning model trained using response information about a normal class. The embodiment will be described below with reference to FIGS. 6 and 7.

In yet another embodiment, the health condition of the diagnosee may be diagnosed using an autoencoder-based deep learning model trained using response information about a patient class. The embodiment will be described below with reference to FIG. 8.

In yet another embodiment, the health condition of the diagnosee may be diagnosed using a classifier that classifies the normal class and the patient class. The embodiment will be described below with reference to FIG. 9.

In yet another embodiment, the health condition (e.g., disease type) of the diagnosee may be diagnosed using a classifier that classifies a disease class. The embodiment will be described below with reference to FIG. 10.

In yet another embodiment, the diagnosis may be performed based on a combination of the embodiments described above. For example, the diagnosis system 10 may also diagnose the health condition of the diagnosee by using a first deep learning model trained with response information about the normal class and a second deep learning model trained with response information of the patient class together. As another example, the diagnosis system 10 may also diagnose the health condition of the diagnosee using a classifier that classifies a normal class and a disease class. As yet another example, the diagnosis system 10 may diagnose the presence or absence of the disease of the diagnosee using the first deep learning model trained with the response information from the normal class, and also diagnose a disease type of the diagnosee using a classier that classifies the disease class in response to the diagnosis result that the disease is present.

In step S24, the diagnosis result may be provided to the diagnosee. For example, the diagnosis system 10 may provide the diagnosis result to the diagnosee terminal 1.

The diagnosis result may include information such as the health condition (e.g., presence or absence of disease, type of disease) of the diagnosee, a treatment method, etc. However, the present disclosure is not limited thereto. Examples of the treatment method will refer to Tables 5 to 7 below. Tables 5 to 7 illustrate life regimens to treat problems with the energy and blood generation, circulation, and balance adjustment functions, respectively.

TABLE 5

| Classification | Life regimens |
| --- | --- |
| Food | Eat three meals slowly at a set time. |
| | Avoid oily food, flour-based food, and cold food. |
| | Eat soft and warm foods. |
| | Drink ginseng tea, ginger tea, cinnamon tea, mugwort tea, etc., which help with a stomach function. |
| Exercise | Avoid strenuous exercise and do exercises such as stretching, yoga, and walking. |
| | Because a lack of energy and blood can lead to obesity in the lower body, do upper body exercises (e.g., horizontal bar, upper body dumbbell exercises) that can draw energy upward. |
| | Avoid exercising in cold water, such as swimming. |
| Hobby | Try to live a bright life by intentionally listening to upbeat music. |

TABLE 6

| Classification | Life regimens |
| --- | --- |
| Food | When there is a problem with the circulation function, there is a tendency for metabolic products to accumulate in the body, so that the amount of food is controlled to manage obesity. |
| | Eat mainly a low-carbohydrate, high-protein diet. |
| | Drink teas that help with the circulation function, such as Ophiopogon japonicus tea, mulberry leaf tea, yulmu tea, and green tea. |
| Exercise | Avoid continuously lying down or napping for 30 minutes or more because of being tired. |
| | Do exercise that sweats a lot, such as brisk walking, jogging, hiking, or swimming. |
| | In obese states, the amount of exercise increases along with fat loss. |
| Hobby | Do active and dynamic activities, such as aerobics, dance sports, and nanta. |
| | Enjoy listening to exciting dance music, etc. |

TABLE 7

| Classification | Life regimens |
| --- | --- |
| Food | Drink plenty of water of about 2 liters a day to avoid lack of yin energy. |
| | Eat fish, seaweed, and cold foods, and avoid spicy and salty foods or dry side dishes. |
| | Drink barley tea, which has a cool nature, and Chinese matrimony vina tea, eucommia tea, cornelian cherry tea, etc. which strengthen the yin energy, and avoid teas such as coffee or green tea that stimulate and enhance the body due to caffeine. |
| Exercise | Avoid exercise that causes a lot of sweating. |
| | Since a lower body will be weak due to a lack of yin energy, do lower body exercises that can draw the energy downward (e.g., riding a bicycle, walking barefoot, walking backwards, climbing stairs, squats, etc.). |
| | Avoid swimming or other upper body exercises that do not apply gravity to the lower body. |
| Hobby | Do static activities, such as meditation, danjeon |

TABLE 7-continued

| Classification | Life regimens |
| --- | --- |
| | breathing, art, and baduk. |
| | Listen to quiet, relaxing music. |

So far, a survey-based diagnosis method according to several embodiments of the present disclosure has been described with reference to FIG. 2. According to the method described above, it is possible to diagnose the health condition of a diagnosee using a plurality of survey questions for diagnosing energy and blood generation function, circulation function, and balance adjustment function. From an oriental medicine viewpoint, since most diseases are caused by problems with the functions, it is possible to accurately diagnose the health condition of a diagnosee by using survey questions for diagnosing these functions. Furthermore, it is possible to provide a quick and convenient diagnosis service to a diagnosee by using a survey technique.

Hereinafter, several embodiments of a diagnosis method will be described with reference to the drawings in FIG. 3 and below.

First, a diagnosis method according to an embodiment of the present disclosure will be described with reference to FIGS. 3 and 4.

As illustrated in FIG. 3, the embodiment relates to a method for diagnosing a health condition of a diagnosee based on vector similarity, and may start at step S222 of generating a state vector representing the health condition of the diagnosee based on response information about the diagnosee. A specific method of generating the state vector at step S222 may vary.

For example, the diagnosis system 10 may generate a state vector for the energy and blood generation function based on the scores of the first survey question. As a more specific example, if the first survey question consists of a plurality of questions, a state vector (e.g., a vector having the scores of the response items of the diagnosee as a vector element) for the energy and blood generation function may be generated based on the scores of each question. Further, the diagnosis system 10 may generate a state vector for the energy and blood circulation function based on the scores of the second survey question, and generate a state vector for the energy and blood balance adjustment function based on the scores of the third survey question.

As another example, as illustrated in FIG. 4, the diagnosis system 10 may generate vectors V1 to V3 for the first survey question to third survey question 41 to 43 and generate a state vector $V_{state}$ by synthesizing the generated state vector based on predetermined weights W1 to W3. In such a case, a state vector $V_{state}$ may be generated by comprehensively considering the energy and blood generation function, circulation function, and balance adjustment function. In this example, the weights W1 to W3 may also vary depending on the demographic characteristics (e.g., sex, age range, age, race, body type, BMI, etc.) of the diagnosee and disease history (e.g., type of disease, number of times suffering from a disease, etc.). For example, since the energy and blood generation function is closely related to the stomach, if there is a history of diseases related to the stomach, the weight W1 for the first survey question may be determined as a higher value. Similarly, when there is a history of cardiopulmonary diseases, the weight W2 for the second survey question may be determined as a higher value. Alternatively, in the case of a lower body obesity body type, since there is a high possibility of having a problem with the energy and blood generation function, the weight for the first survey question may be determined as a higher value. Similarly, in the case of an upper body obesity body type, since there is a high possibility of having a problem with the energy and blood balance adjustment function, the weight for the third survey question may be determined as a higher value. Alternatively, since there is a high possibility of having a problem with the energy and blood circulation function due to a decreased metabolism as the age is higher, the weight for the second survey question may be determined as a higher value as the age range of the diagnosee increases.

As yet another example, as illustrated in FIG. 5, the diagnosis system 10 may generate a state vector using an autoencoder-based deep learning model. Specifically, the state vector may be generated using a latent vector 53 extracted from an encoder 52 of a deep learning model trained with response information about a normal class or a patient class. The autoencoder-based deep learning model may include a basic auto-encoder and its variations (e.g., variational autoencoders). However, for the convenience of understanding, the following description will continue assuming that the deep learning model consists of a basic autoencoder structure. This example will be further described with reference to FIG. 5. FIG. 5 illustrates an autoencoder structure in which a dimensionality d of the latent vector 53 (or bottleneck layer) is 3.

As illustrated in FIG. 5, an autoencoder-based deep learning model may consist of an encoder 52 and a decoder 54, and may be trained based on a reconstruction loss value between input data 51 and output data 55. Those skilled in the art have already known the configuration and operating principle of the autoencoder, and thus, more description of the autoencoder will be omitted.

In this example, the diagnosis system 10 may extract the latent vector 53 by inputting response information about the diagnosee into the encoder 52 of the deep learning model trained with the response information about the normal class or the patient class. Of course, the diagnosis system 10 may convert the response information about the diagnosee into a numerical form to be input to the encoder 52 through an appropriate vectorization technique (e.g., the method described with reference to FIG. 4). In addition, the diagnosis system 10 may generate a state vector by using the extracted latent vector 53 as a state vector of the diagnosee, or performing additional processing (e.g., PCA, etc.) on the extracted latent vector 53.

It will be described with reference to FIG. 3 again.

In step S224, the health condition of the diagnosee may be diagnosed based on the similarity between the generated state vector and a disease vector. For example, as illustrated in FIG. 4, the diagnosis system 10 may diagnose whether there is an abnormality in the health condition or a type of disease based on the similarity (e.g., cosine similarity, etc.) between the state vector $V_{state}$ of the diagnosee and disease vectors $V_{diseaseA}$ and $V_{diseaseB}$ (e.g., diagnose a disease with the highest similarity as the disease of the diagnosee).

For reference, the disease vectors $V_{diseaseA}$ and $V_{diseaseB}$ may be generated based on response information about patients belonging to the corresponding disease class, and may be generated in the same or similar manner as the generated vector.

So far, the diagnosis method according to an embodiment of the present disclosure has been described with reference to FIGS. 3 to 5. Hereinafter, a diagnosis method according to another embodiment of the present disclosure will be described with reference to FIG. 6.

As illustrated in FIG. 6, the embodiment relates to a method for diagnosing a health condition of a diagnosee using an autoencoder-based deep learning model 60 trained with response information 63 about a normal class (see normal).

Specifically, the deep learning model 60 may be configured to include an encoder 61 and a decoder 62, and may be trained using response information 63 of a normal class. For example, the diagnosis system 10 may input individual response information 64 into the deep learning model 60 and train the deep learning model 60 using the reconstruction loss value between input information 64 and reconstructed information 65 (e.g., the individual response information 64 may be converted into a numerical form and input into the deep learning model 60; see FIG. 12). At this time, in the deep learning model 60, a process of encoding the input information 64 into a latent vector by the encoder 61 and decoding the latent vector by the decoder 62 may be performed, and as the reconstruction loss value is back-propagated, weight parameters of the encoder 61 and the decoder 62 may be updated. As such a training process is repeated, the deep learning model 60 has the ability to compress (encode) and then reconstruct (decode) response information (e.g., 64) of the normal class.

Next, as illustrated in FIG. 7, a reconstruction loss value for response information 71 about the diagnosee may be calculated using the trained deep learning model 60. As described above, the reconstruction loss value may be calculated based on a difference between the response information 71 about the diagnosee and information 72 reconstructed by the deep learning model 60.

Next, the health condition of the diagnosee may be diagnosed based on the calculated reconstruction loss value. For example, if the reconstruction loss value is equal to or greater than a reference value, the diagnosis system 10 may determine that there is an abnormality in the health condition of the diagnosee. A large reconstruction loss value means that the response information 71 about the diagnosee is information that is not well reconstructed by the deep learning model 60, which is because the response information 71 about the diagnosee is significantly different from the response information 63 about the normal class. If the reconstruction loss value is equal to or less than the reference value, the diagnosis system 10 may determine that there is no abnormality in the health condition of the diagnosee.

So far, the diagnosis method according to another embodiment of the present disclosure has been described with reference to FIGS. 6 and 7. Hereinafter, a diagnosis method according to yet another embodiment of the present disclosure will be described with reference to FIG. 8.

As illustrated in FIG. 8, the embodiment relates to a method for diagnosing a health condition of a diagnosee using an autoencoder-based deep learning model 80 trained with response information 83 about a patient class (see disease).

Specifically, the deep learning model 80 may be configured to include an encoder 81 and a decoder 82, and may be trained using response information 83 about a patient class. For example, the diagnosis system 10 may input individual response information 84 into the deep learning model 80 and train the deep learning model 80 using a reconstruction loss value between input information 84 and reconstructed information 85.

Next, a reconstruction loss value for the response information (e.g., 71) about the diagnosee may be calculated using the trained deep learning model 80, and the health condition of the diagnosee may be diagnosed based on the calculated reconstruction loss value. For example, if the reconstruction loss value is equal to or greater than a reference value, the diagnosis system 10 may determine that there is no abnormality in the health condition of the diagnosee. A large reconstruction loss value means that the response information (e.g., 71) about the diagnosee is information that is not well reconstructed by the deep learning model 80, which is because the response information (e.g., 71) about the diagnosee is significantly different from the response information 83 about the patient class. If the reconstruction loss value is equal to or less than the reference value, the diagnosis system 10 may determine that there is an abnormality in the health condition of the diagnosee.

So far, the diagnosis method according to yet another embodiment of the present disclosure has been described with reference to FIG. 8. Hereinafter, a diagnosis method according to yet another embodiment of the present disclosure will be described with reference to FIG. 9.

As illustrated in FIG. 9, the embodiment relates to a method for diagnosing a health condition of a diagnosee using an autoencoder-based deep learning model 90 trained with response information 95 about a normal class (see normal) and a patient class (see disease).

Specifically, the deep learning model 90 may be configured to include an encoder 91, a decoder 92, and a classifier 93. At this time, the classifier 93 may serve to classify an input latent vector 94 into a normal class and a patient class.

As described above, the deep learning model 90 may be trained using response information 95 about the normal class and the patient class. For example, the diagnosis system 10 may train the encoder 91 and decoder 92 using a reconstruction loss value for individual response information 96 about the normal class or the patient class. The reconstruction loss value may be calculated based on a difference between input response information 96 and reconstructed information 97. In addition, the diagnosis system 10 may input a latent vector 94 extracted from the input response information 96 into the classifier 93 to calculate a classification loss value for the latent vector 94. The classification loss value may be calculated based on a difference between a predicted class and a correct class (i.e., a difference in confidence scores for each class) by the classifier 93. In addition, the diagnosis system 10 may train the classifier 93 and the encoder 91 using the classification loss value while freezing the decoder 92. Accordingly, the encoder 91 may be trained to extract a latent vector 94 suitable for class classification.

Next, a latent vector (e.g., 94) may be extracted from the response information (e.g., 71) of the diagnosee using the trained deep learning model 90, and a confidence score for each class (e.g., a confidence score for a normal class or a patient class) for the latent vector (e.g., 94) may be calculated by the classifier 93.

Next, the health condition of the diagnosee may be diagnosed based on the confidence score for each class. For example, if the confidence score of the patient class is equal to or greater than a reference value (or the confidence score of the normal class is equal to or less than a reference value), the diagnosis system 10 may determine that there is an abnormality in the health condition of the diagnosee. If it is visa verse, the diagnosis system 10 may determine that there is no abnormality in the health condition of the diagnosee.

So far, the diagnosis method according to yet another embodiment of the present disclosure has been described with reference to FIG. 9. Hereinafter, a diagnosis method according to yet another embodiment of the present disclosure will be described with reference to FIG. 10.

As illustrated in FIG. 10, the embodiment relates to a method for diagnosing a disease type of a diagnosee using an autoencoder-based deep learning model 100 trained with response information 105 about patients in different disease classes (see disease A and disease B).

Specifically, the deep learning model 100 may be configured to include an encoder 101, a decoder 102, and a classifier 103. At this time, the classifier 103 may serve to classify an input latent vector 104 into a first disease class (see disease A) and a second disease class (see disease B). Of course, the classifier 103 may further perform classification for a third disease class.

As described above, the deep learning model 100 may be trained using response information 105 about patients belonging to different disease classes. For example, the diagnosis system 10 may train the encoder 101 and decoder 102 using a reconstruction loss value for individual response information 106 about a patient in a specific disease class. The reconstruction loss value may be calculated based on a difference between input response information 106 and reconstructed information 107. In addition, the diagnosis system 10 may input a latent vector 104 extracted from the input response information 106 into the classifier 103 to calculate a classification loss value for the latent vector 104. The classification loss value may be calculated based on a difference between a predicted disease class and a correct class (i.e., a difference in confidence scores for each class) by the classifier 103. In addition, the diagnosis system 10 may train the classifier 103 and the encoder 101 using the classification loss value while freezing the decoder 102. Accordingly, the encoder 101 may be trained to extract a latent vector 104 suitable for disease class classification.

Next, a latent vector (e.g., 104) may be extracted from the response information (e.g., 71) of the diagnosee using the trained deep learning model 100, and a confidence score for each disease class for the latent vector (e.g., 104) may be calculated by the classifier 103.

Next, the disease type of the diagnosee may be diagnosed based on the confidence score for each class. For example, when the confidence score of the first disease class is equal to or greater than a reference value, the diagnosis system 10 may determine that the diagnosee suffers from a first disease.

So far, several embodiments of the diagnosis method have been described with reference to FIGS. 3 to 10. According to the aforementioned method, the health condition of the diagnosee may be accurately diagnosed using the autoencoder-based deep learning model trained using similarity in a vector space or using response information about the normal class or the patient class. Furthermore, the type of disease may be accurately diagnosed by using a classifier that classifies disease classes.

Meanwhile, there may be cases where there are missing values (i.e., non-response to specific survey items) in the response information provided by the diagnosee for various reasons. In such a case, the diagnosis system 10 may request the diagnosee to correct the missing values, or may perform automatic missing value correction for the convenience of the diagnosee. Hereinafter, a method for performing automatic missing value correction by the diagnosis system 10 will be described in detail with reference to FIGS. 11 and 12.

FIG. 11 is an exemplary flowchart illustrating a missing value correction method according to an embodiment of the present disclosure. However, it is only a preferred embodiment for achieving the object of the present disclosure, and it is obvious that some steps may be added or deleted as necessary.

As illustrated in FIG. 11, the embodiment may start at step S110 of acquiring an autoencoder-based deep learning model trained using response information about a survey respondent. For example, as illustrated in FIG. 12, the diagnosis system 10 consists of an encoder 121 and a decoder 122 and may acquire a deep learning model 120 trained with response information.

In an example, classes of survey respondents may be classified based on demographic characteristics and/or disease history, and a deep learning model for each class may be constructed. For example, a first deep learning model may be constructed using response information about a survey respondent belonging to a first class, and a second deep learning model may be constructed using response information about a survey respondent belonging to a second class. In this case, the diagnosis system 10 may determine a model matching the diagnosee among a plurality of deep learning models to be used to correct missing values. For example, the diagnosis system 10 may use a deep learning model that matches the demographic characteristics and/or disease history of the diagnosee, thereby further improving the accuracy of missing value correction.

In step S112, a specific value may be allocated to a missing value of the response information about the diagnosee. For example, as illustrated in FIG. 12, the diagnosis system 10 may allocate a specific value to a missing value 124 existing in response information 123 about the diagnosee. The specific value may be a representative response value (e.g., mean, median, mode, etc.), a zero value, a random value, etc. of survey respondents with the same (or similar) demographic characteristics and/or disease history as the diagnosee, but is not limited thereto.

If step S112 is performed repeatedly, a different value than before may be allocated to the missing value. For example, the diagnosis system 10 may allocate a different random value than before or allocate a new value in a direction of decreasing a reconstruction loss value (e.g., if the reconstruction loss value decreases as the missing value 124 decreases, a smaller value than before is allocated).

In step S114, a reconstruction loss value may be calculated using the trained deep learning model. For example, as illustrated in FIG. 12, the diagnosis system 10 may input response information 123 filled with missing values 124 into the deep learning model 120 to calculate the reconstruction loss value. At this time, the response information 123 is converted into numerical data 125 through an appropriate vectorization technique, and the reconstruction loss value may be calculated based on a difference between input data 125 and reconstructed data 126.

In step S116, it may be determined whether the reconstruction loss value is less than or equal to a reference value. Depending on the determination result, step S118 may also be performed, and steps S112 to S116 may also be performed again.

The reference value may be a fixed value or a variable value that changes depending on a situation. For example, the reference value may be a variable value that varies depending on the demographic characteristics and/or disease history of the diagnosee. As a more specific example, if the diagnosee has disease history, the reference value may be set to a lower value than in other cases to more strictly correct the missing value. In the opposite case, the reference value may be set to a larger value than in other cases. As another example, even if the age of the diagnosee is elderly, the reference value may be set to a lower value than in other cases. In the opposite case, the reference value may be set to a larger value than in other cases.

In an embodiment, steps S112 to S116 may be repeatedly performed until a specified termination condition is satisfied. For example, the diagnosis system 10 may repeat the above-described steps while changing the allocation value until the reconstruction loss value becomes less than or equal to the reference value. Alternatively, the diagnosis system 10 may repeat the above-described steps until a specified number of repetitions is reached, and when the reconstruction loss value below the reference value is not calculated and the specified number of repetitions is exceeded, the diagnosis system 10 may also request the diagnosee to correct the missing value.

In step S118, the missing value may be corrected to an allocated value.

So far, the missing value correction method according to an embodiment of the present disclosure has been described with reference to FIGS. 11 and 12. According to the above-described method, missing value correction may be accurately performed by using the autoencoder-based deep learning model 120 that has trained the characteristics of response information.

Hereinafter, an exemplary computing device 130 capable of implementing the diagnosis system 10 according to several embodiments of the present disclosure will be described with reference to FIG. 13.

FIG. 13 is an exemplary hardware configuration diagram illustrating the computing device 130.

As illustrated in FIG. 13, the computing device 130 may include one or more processors 131, a bus 133, a communication interface 134, a memory 132 that loads a computer program executed by the processors 131, and a storage 135 that stores a computer program 136. However, only the components related to the embodiment of the present disclosure are illustrated in FIG. 13. Accordingly, those of ordinary skill in the art to which the present disclosure pertains may see that other general-purpose components other than components illustrated in FIG. 13 may be further included. That is, the computing device 130 may further include various components in addition to the components illustrated in FIG. 13. In addition, in some cases, the computing device 130 may also be configured in a form in which some of the components illustrated in FIG. 13 are omitted. Hereinafter, each component of the computing device 130 will be described.

The processor 131 may control the overall operation of each component of the computing device 130. The processor 131 may be configured to include at least one of a central processing unit (CPU), a micro processor unit (MPU), a micro controller unit (MCU), a graphic processing unit (GPU) or any type of processor well-known in the art. Further, the processor 131 may perform an operation of at least application or program for executing the operation/method according to the embodiments of the present disclosure. The computing device 130 may provide one or more processors.

Next, the memory 132 may store various types of data, instructions, and/or information. The memory 132 may load a computer program 136 from the storage 135 in order to execute the operation/method according to the embodiments of the present disclosure. The memory 132 may be implemented as a volatile memory such as RAM, but the technical scope of the present disclosure is not limited thereto.

Next, the bus 133 may provide a communication function between components of the computing device 130. The bus 133 may be implemented as various types of buses, such as an address bus, a data bus, and a control bus.

Next, the communication interface 134 may support wired and wireless Internet communication of the computing device 130. In addition, the communication interface 134 may also support various communication schemes in addition to the internet communication. To this end, the communication interface 134 may be configured to include a communication module well-known in the art.

Next, the storage 135 may non-temporarily store one or more computer programs 136. The storage 135 may be configured to include a nonvolatile memory such as a read only memory (ROM), an erasable programmable ROM (EPROM), an electrically erasable programmable ROM (EEPROM), a flash memory or the like, a hard disk, a removable disk, or any type of computer-readable recording medium well-known in the art to which the present disclosure pertains.

Next, the computer program 136 may include one or more instructions that allow the processor 131 to perform the operations/methods according to various embodiments of the present disclosure when loaded into the memory 132. That is, the processor 131 may perform operations/methods according to various embodiments of the present disclosure by executing the one or more of the instructions.

For example, the computer program 136 may include one or more instructions for performing an operation of acquiring response information about a diagnosee with respect to a plurality of survey questions and an operation of performing a diagnosis on the diagnosee based on the acquired response information. In such a case, the diagnosis system 10 according to several embodiments of the present disclosure may be implemented through the computing device 130.

So far, the exemplary computing device 130 capable of implementing the diagnosis system 10 according to several embodiments of the present disclosure has been described with reference to FIG. 13.

So far, the technical idea of the present disclosure described with reference to FIGS. 1 to 13 may be implemented as computer-readable codes on a computer-readable medium. The computer-readable recording medium may be, for example, a removable recording medium (CD, DVD, Blu-ray disc, USB storage device, removable hard disk) or a fixed recording medium (ROM, RAM, computer-attached hard disk). The computer program recorded on the computer-readable recording medium may be transmitted to another computing device via a network such as the Internet and installed on the another computing device, thereby being used on the another computing device.

Hereinabove, even though it has been described that all of components constituting the embodiment of the present disclosure are coupled as a single unit or coupled to be operated as the single unit, the technical idea of the present disclosure is not necessarily limited to these embodiments. That is, one or more of all of the components may be selectively coupled to be operated within the scope of the object of the present disclosure.

Although operations are illustrated in the drawings in a particular order, it should not be understood to mean that the operations need to be performed in the illustrated particular order or in a sequential order, or that all of the illustrated operations need to be performed to obtain desired results. In a certain situation, multitasking and parallel processing may be advantageous. Moreover, in the embodiments described above, it should not be understood that the separation of the various components is not necessarily required, and it should be understood that the described program components and systems may generally be integrated together into a single software product or packaged into a plurality of software products.

Hereinabove, the embodiments of the present disclosure have been described with the accompanying drawings, but it may be understood by those skilled in the art that the present disclosure may be executed in other detailed forms without changing the technical idea or requisite features of the present disclosure. Therefore, it should be appreciated that the aforementioned embodiments described above are illustrative in all aspects and are not restricted. The protection scope of the present disclosure should be interpreted by the appended claims and all technical ideas in the equivalent range thereto should be interpreted to be included in the claims of the technical idea defined by the present disclosure.

The invention claimed is:

1. A survey-based diagnosis method performed by at least one computing device comprising:

acquiring response information about a diagnosee with respect to a plurality of survey questions, wherein the plurality of survey questions include a first survey question for diagnosing an energy and blood generation function, a second survey question for diagnosing an energy and blood circulation function, and a third survey question for diagnosing an energy and blood balance adjustment function; and performing a diagnose on the diagnosee based on the acquired response information, wherein the performing of the diagnosis comprises Steps (i) or Steps (ii):

Steps (i):

acquiring a first autoencoder-based deep learning model trained using response information about a normal class and a patient class with respect to the plurality of survey questions, wherein the first autoencoder-based deep learning model includes a first encoder, a first decoder, and a first classifier for classifying the normal class and the patient class, the first encoder and the first decoder are trained based on a first reconstruction loss value, and the first encoder is further trained based on a first classification loss value of the first classifier for a first latent vector while the first decoder is frozen;

extracting the first latent vector for the acquired response information by the first encoder;

acquiring a first confidence score for each class for the extracted first latent vector by the first classifier; and diagnosing the health condition of the diagnosee based on the acquired first confidence score, Steps (ii):

acquiring a second autoencoder-based deep learning model trained using response information about the patient class with respect to the plurality of survey questions, wherein the patient class consists of patients in a first disease class and a second disease class, the first disease class is a different disease class from the second disease class, the second autoencoder-based deep learning model includes a second encoder, a second decoder, and a second classifier for classifying the first disease class and the second disease class, the second encoder and the second decoder are trained based on a second reconstruction loss value, and the second encoder is further trained based on a second classification loss value of the second classifier for a second latent vector while the second decoder is frozen;

extracting the second latent vector for the acquired response information by the second encoder;

acquiring a second confidence score for each class for the extracted second latent vector by the second classifier; and diagnosing a disease type of the diagnosee based on the acquired second confidence score.

2. The survey-based diagnosis method of claim 1, wherein the performing of the diagnosis comprises generating a state vector representing a health condition of the diagnosee based on the response information; and diagnosing the health condition of the diagnosee based on similarity between the generated state vector and a disease vector.

3. The survey-based diagnosis method of claim 2, wherein the generating of the state vector comprises generating a vector for each survey question based on scores of the first survey question to the third survey question; and generating the state vector by synthesizing the generated vector based on a weight for each survey question, wherein the weight varies depending on demographic characteristics and disease history of the diagnosee.

4. The survey-based diagnosis method of claim 2, wherein the generating of the state vector comprises acquiring an autoencoder-based deep learning model trained using response information about a patient class with respect to the plurality of survey questions;

extracting a latent vector for the acquired response information using the acquired deep learning model; and generating the state vector based on the extracted latent vector.

5. The survey-based diagnosis method of claim 1, wherein the performing of the diagnosis comprises acquiring an autoencoder-based deep learning model trained using response information about a normal class with respect to the plurality of survey questions;

calculating a reconstruction loss value for the acquired response information using the acquired deep learning model; and diagnosing the health condition of the diagnosee based on the calculated reconstruction loss value.

6. The survey-based diagnosis method of claim 1, wherein the acquired response information includes a missing value for a specific survey question, and the performing of the diagnosis comprises acquiring an autoencoder-based deep learning model trained using response information with respect to the plurality of survey questions;

allocating a specific value to the missing value;

calculating a reconstruction loss value for the response information allocated with the specific value using the acquired deep learning model;

correcting the missing value to the specific value in response to the determination that the calculated reconstruction loss value is less than or equal to a reference value; and performing the correction of the diagnosee based on the response information with the corrected missing value.

7. The survey-based diagnosis method of claim 6, wherein the acquiring of the deep learning model comprises acquiring a first deep learning model trained using response information about a first class and a second deep learning model trained using response information about a second class with respect to the plurality of survey questions, wherein the first class is a survey respondent class having different demographic characteristics from the second class; and determining a deep learning model that matches the demographic characteristics of the diagnosee in the first deep learning model and the second deep learning model.

8. A survey-based diagnosis system comprising:

one or more processors; and a memory for storing one or more instructions, wherein the one or more processors execute one or more of the stored instructions to perform an operation of acquiring response information about a diagnosee with respect to a plurality of survey questions, wherein the plurality of survey questions include a first survey question for diagnosing an energy and blood generation function, a second survey question for diagnosing an energy and blood circulation function, and a third survey question for diagnosing an energy and blood balance adjustment function; and an operation of performing a diagnosis for the diagnosee based on the acquired response information, wherein the performing of the diagnosis comprises Steps (i) or Steps (ii):

Steps (i):

acquiring a first autoencoder-based deep learning model trained using response information about a normal class and a patient class with respect to the plurality of survey questions, wherein the first autoencoder-based deep learning model includes a first encoder, a first decoder, and a first classifier for classifying the normal class and the patient class, the first encoder and the first decoder are trained based on a first reconstruction loss value, and the first encoder is further trained based on a first classification loss value of the first classifier for a first latent vector while the first decoder is frozen;

extracting the first latent vector for the acquired response information by the first encoder;

acquiring a first confidence score for each class for the extracted first latent vector by the first classifier; and diagnosing the health condition of the diagnosee based on the acquired first confidence score, Steps (ii):

acquiring a second autoencoder-based deep learning model trained using response information about a patient class with respect to the plurality of survey questions, wherein the patient class consists of patients in a first disease class and a second disease class, the first disease class is a different disease class from the second disease class, the second autoencoder-based deep learning model includes a second encoder, a second decoder, and a second classifier for classifying the first disease class and the second disease class, the second encoder and the second decoder are trained based on a second reconstruction loss value, and the second encoder is further trained based on a second classification loss value of the second classifier for a second latent vector while the second decoder is frozen;

extracting the second latent vector for the acquired response information by the second encoder;

acquiring a second confidence score for each class for the extracted second latent vector by the second classifier; and diagnosing a disease type of the diagnosee based on the acquired second confidence score.

9. A computer program connected with a computing device and stored in a non-transitory computer-readable recording medium to execute steps of:

acquiring response information about a diagnosee with respect to a plurality of survey questions, wherein the plurality of survey questions include a first survey question for diagnosing an energy and blood generation function, a second survey question for diagnosing an energy and blood circulation function, and a third survey question for diagnosing an energy and blood balance adjustment function; and performing a diagnosis for the diagnosee based on the acquired response information, wherein the performing of the diagnosis comprises Steps (i) or Steps (ii):

Steps (i):

acquiring a first autoencoder-based deep learning model trained using response information about a normal class and a patient class with respect to the plurality of survey questions, wherein the first autoencoder-based deep learning model includes a first encoder, a first decoder, and a first classifier for classifying the normal class and the patient class, the first encoder and the first decoder are trained based on a first reconstruction loss value, and the first encoder is further trained based on a first classification loss value of the first classifier for a first latent vector while the first decoder is frozen;

extracting the first latent vector for the acquired response information by the first encoder;

acquiring a first confidence score for each class for the extracted first latent vector by the first classifier; and diagnosing the health condition of the diagnosee based on the acquired first confidence score, Steps (ii):

acquiring a second autoencoder-based deep learning model trained using response information about a patient class with respect to the plurality of survey questions, wherein the patient class consists of patients in a first disease class and a second disease class, the first disease class is a different disease class from the second disease class, the second autoencoder-based deep learning model includes a second encoder, a second decoder, and a second classifier for classifying the first disease class and the second disease class, the second encoder and the second decoder are trained based on a second reconstruction loss value, and the second encoder is further trained based on a second classification loss value of the second classifier for a second latent vector while the second decoder is frozen;

extracting the second latent vector for the acquired response information by the second encoder;

acquiring a second confidence score for each class for the extracted second latent vector by the second classifier; and diagnosing a disease type of the diagnosee based on the acquired second confidence score.

* * * * *